US008680357B1

(12) United States Patent
Rokicki et al.

(10) Patent No.: US 8,680,357 B1
(45) Date of Patent: Mar. 25, 2014

(54) DEHYDROGENATION CATALYST

(75) Inventors: Andrzej Rokicki, Prospect, KY (US); Vladimir Fridman, Louisville, KY (US)

(73) Assignee: Clariant Corporation, Louisville, KY (US)

( * ) Notice: Subject to any disclaimer, the term of this patent is extended or adjusted under 35 U.S.C. 154(b) by 1299 days.

(21) Appl. No.: 10/968,456

(22) Filed: Oct. 19, 2004

Related U.S. Application Data

(62) Division of application No. 10/047,598, filed on Jan. 14, 2002, now abandoned.

(51) Int. Cl.
*C07C 5/333* (2006.01)

(52) U.S. Cl.
USPC .................................................. 585/663

(58) Field of Classification Search
USPC .................................................. 585/663
See application file for complete search history.

(56) References Cited

U.S. PATENT DOCUMENTS

| | | | |
|---|---|---|---|
| 2,300,971 A | 11/1942 | Roberts | |
| 2,374,404 A | 4/1945 | Ahlberg | |
| 2,375,402 A | 5/1945 | Corson | |
| 2,399,678 A | 5/1946 | Houdry | |
| 2,423,029 A | 6/1947 | Houdry | |
| 2,943,067 A | 6/1960 | Sieg | |
| 2,945,823 A | 7/1960 | Cornelius | |
| 2,956,030 A | 10/1960 | Cornelius | |
| 2,973,330 A * | 2/1961 | Kant et al. | 502/334 |
| 2,985,596 A | 5/1961 | Pitzer | |
| 3,202,725 A * | 8/1965 | Waldemar et al. | 585/315 |
| 3,322,849 A | 5/1967 | McEuen | |
| 3,363,023 A | 1/1968 | Mooi | |
| 3,488,402 A | 1/1970 | Michaels | |
| 3,719,721 A | 3/1973 | Hansford | |
| 3,801,672 A | 4/1974 | Bajars | |
| 3,945,946 A | 3/1976 | Hindin | |
| 3,976,034 A | 8/1976 | Shinohara | |
| 4,716,143 A | 12/1987 | Imai | |
| 4,746,643 A | 5/1988 | Buonomo | |
| 4,786,625 A | 11/1988 | Imai | |
| 4,880,764 A | 11/1989 | Imai | |
| 5,378,350 A | 1/1995 | Zimmermann | |
| 5,510,557 A | 4/1996 | Gartside | |
| 6,124,228 A | 9/2000 | Wu | |
| 6,417,422 B1 | 7/2002 | Liu | |

FOREIGN PATENT DOCUMENTS

| | | |
|---|---|---|
| EP | 0947247 | 10/1999 |
| GB | 942944 | 11/1963 |
| GB | 1424382 | 2/1976 |
| WO | WO0168244 | 3/2001 |
| WO | WO2005040075 A1 | 5/2005 |

OTHER PUBLICATIONS

Oberlander, Richard K., Aluminas for Catalysts—Their Preparation and Properties, p. 69 (1983).
Richardson, James T., Principles of Catalyst Development, pp. 35-36 (1989).
Tsuchida, et al., "The effect of $Cr^{3+}$ and $Fe^{3+}$ ions on the transformation of different aluminum hydroxide to alpha—$Al_2O_3$," Thermochimica ACTA, 64, pp. 337-353 (1983).
Office Action dated Jun. 4, 2008 with respect to U.S. Appl. No. 11/129,834.
Office Action dated Aug. 7, 2003 with respect to U.S. Appl. No. 10/047,598.
Office Action dated Mar. 22, 2004 with respect to U.S. Appl. No. 10/047,598.
Final Office Action dated Jul. 20, 2004 with respect to U.S. Appl. No. 10/047,598.
Advisory Action dated Sep. 30, 2004 with respect to U.S. Appl. No. 10/047,598.
Response filed Sep. 3, 2008 to Office Action dated Jun. 4, 2008 with respect to U.S. Appl. No. 11/129,834.
Rokicki, Andrzej, Catalyst in Petroleum Refining and Petrochemicals, Proceeding of the Saudi-Japanese Symposium, 11th, Dhahran, Saudi Arabia, Nov. 11-12, 2001.
Response filed Mar. 6, 2009 to Notice dated Feb. 10, 2009 regarding U.S. Appl. No. 11/129,834.
Final Office Action dated Oct. 8, 2008 with respect to U.S. Appl. No. 11/129,834.

* cited by examiner

*Primary Examiner* — Stuart Hendrickson
(74) *Attorney, Agent, or Firm* — McDonnell Boehnen Hulbert & Berghoff LLP

(57) ABSTRACT

A process for the dehydrogenation of a hydrocarbon feed stream, wherein the hydrocarbon feed stream substantially includes hydrocarbons containing 3 to 5 carbon atoms, wherein the process includes passing the hydrocarbon feed stream over a dehydrogenation catalyst containing from about 50 to about 90 percent by weight of an eta alumina carrier, about 10 to about 30 percent by weight of chromia and from about 0.1 to about 5 percent by weight of zirconia added as a stabilizing material.

17 Claims, No Drawings

DEHYDROGENATION CATALYST

CROSS REFERENCE TO RELATED APPLICATIONS

This application is a divisional application based on application Ser. No. 10/047,598, filed on Jan. 14, 2002 now abandoned.

BACKGROUND OF INVENTION

1. Field of Invention

This invention relates to processes for the dehydrogenation of hydrocarbon feed streams, particularly C3 to C5 alkane hydrocarbon feed streams, using a particular chromia-eta alumina catalyst. The invention more specifically relates to processes for the dehydrogenation of light alkane hydrocarbon feed streams using a stabilized chromia alumina catalyst containing a zirconium additive, wherein the alumina is eta alumina.

2. Prior Art

Alkane dehydrogenation is a recognized process for production of a variety of useful hydrocarbon products, such as isobutylene for conversion to MTBE, isooctane and alkylates to supplement and enrich gasolines and propylene for use in the polymer industry. There are several current catalytic processes useful for catalytic dehydrogenation of light alkanes, including the Süd-Chemie CATOFIN® process, the Linde/BSF process, UOP's Oleflex® process, Phillips' Star™ process and the Snamprogetti-Yarsintee process. The catalysts that are used in these processes are manufactured from two different groups of materials. The Süd-Chemie CATOFIN® process, the Linde/BSF process and the Snamprogetti-Yarsintee process utilize chromia-alumina catalysts. In contrast, the catalysts for the UOP and Phillips processes comprise precious metal(s) on support catalysts, as disclosed for example in U.S. Pat. Nos. 4,880,764, 4,786,625 and 4,716,143.

Chromia-alumina dehydrogenation catalyst technology has been in use for over fifty years as disclosed in U.S. Pat. Nos. 2,423,029, 2,945,823, 2,956,030, 2,985,596, 2,399,678 and GB 942,944. In particular, GB 942,944 discloses a dehydrogenation catalyst for the dehydrogenation of aliphatic hydrocarbons having three to five carbon atoms. The catalyst disclosed by the GB '944 patent was prepared by dehydrating an aluminum trihydrate composition comprising 60 to 100 percent beta alumina trihydrate, heating the resulting dehydrated alumina with steam to adjust its surface area to a range of 100 to 200 $m^2/g$, depositing from about 10 to about 25 percent of $Cr_2O_3$ onto the resulting alumina carrier and steam treating the resulting catalyst at an elevated temperature.

Other chromia-based dehydrogenation catalysts are disclosed in U.S. Pat. Nos. 3,719,721, 4,746,643 and 5,378,350.

With dehydrogenation catalysts used for the above processes, stability of the catalyst plays an important role in the overall efficiency of the dehydrogenation process. Because of the extreme temperature ranges at which the catalytic dehydrogenation procedure is conducted, the life expectancy of the catalyst is often limited. Thus, improving the thermal stability of the catalyst translates into longer catalyst life, allowing for better catalyst utilization and ultimately results in lower consumption of the catalyst during the dehydrogenation process.

One proposed method of stabilizing chromia-alumina dehydrogenation catalysts is by the addition of zirconia as disclosed in U.S. Pat. No. 2,374,404.

In addition, U.S. Pat. No. 2,943,067 discloses an alkali metal promoted, chromia-alumina catalyst with improved stability, wherein the alumina carrier support is derived from a gel alumina. The '067 patent claims improved performance of its aged catalyst for the production of butadiene over the commercially available Harsaw catalyst, which catalyst is produced using a Bayer process alumina for forming the support.

Another group of materials that are used to stabilize an alumina support for dehydrogenation catalysts is siliceous compounds, such as those disclosed in U.S. Pat. No. 2,956,030.

There are a number of different types of alumina that are available for use as the support for dehydrogenation catalysts. However, mid to high surface area, gamma alumina has consistently been the preferred choice as the carrier for such catalysts as disclosed, for example, in U.S. Pat. Nos. 2,956,030, 2,945,823 and 2,374,404.

In particular, gamma alumina is preferred over eta alumina as the carrier material for dehydrogenation catalysts. For example, in Tsuchida, et al., "The effect of $Cr^{3+}$ and $Fe^{3+}$ ions on the transformation of different aluminum hydroxide to alpha-$Al_2O_3$", *Thermochimica ACTA*, 64, pages 337-353 (1983), the preference for gamma alumina over eta alumina is clear. The article states that during the formation of alpha alumina containing $Cr^{3+}$ ions, the transformation of bayerite containing chromium ions from eta alumina to alpha aluminum was "accelerated." In contrast, the transformation of boehmite containing chromium ions from gamma alumina to alpha alumina was "inhibited." Acceleration of this transformation to alpha alumina, as is exhibited by eta alumina, results in reduced stabilization of the catalyst while inhibition in the transformation, as is exhibited by gamma alumina, enhances stabilization of the catalyst end product.

The preference for gamma alumina as the support material for catalysts in general, especially where enhanced stability at higher temperatures is required, is also discussed in Richardson, James T.; *Principles of Catalyst Development*, (1989). The preference for gamma aluminum as a support material is specifically discussed at pages 35 and 36, especially in a situation where a small quantity of zirconia is added to the alumina to stabilize the catalyst.

Another example of the preference for gamma alumina over eta alumina as the material used to form the carrier of a dehydrogenation catalyst is disclosed in U.S. Pat. No. 2,943,067. At column 5, Example 1, the performance of an alumina supported catalyst produced by the Bayer process (which produces a gamma alumina) is described as being superior to a catalyst prepared from a gel-type alumina, which upon heating normally converts to an eta alumina. (Alumina produced by the Bayer process produces gibbsite, which upon heating converts to gamma alumina.) Thus, the '067 patent teaches the superiority of gamma alumina over eta alumina as the carrier for dehydrogenation catalysts.

The lack of thermal stability for catalyst produced from eta alumina is also discussed in Oberlander, Richard K.: *Aluminas for Catalysts—Their Preparation and Properties*, page 69 (1983).

This preference for gamma alumina over eta alumina for catalysts is not surprising because gamma alumina is generally perceived as having a greater thermal stability over eta alumina. In fact, gamma alumina has become the standard alumina utilized for dehydrogenation catalysts. (The market has accepted this principle as gamma alumina is readily available in the market while eta alumina is sparsely available, if at all.)

Although dehydrogenation catalysts prepared from chromia-alumina catalysts have been extensively employed for many years, there are still problems with current catalysts, especially their thermal stability. Even when these catalysts are stabilized by the addition of an additive, such as a zirconium or a silicon compound, these catalysts still show limited stability because of the severity of the operating conditions, particularly the high temperature, during the dehydrogenation procedure.

Accordingly, it is an object of the invention to disclose processes for the dehydrogenation of hydrocarbon feed streams, particularly aliphatic hydrocarbon feed streams, wherein the hydrocarbons preferably contain 3 to 5 carbon atoms, utilizing an improved chromia-alumina catalyst, wherein the alumina utilized in the catalyst is eta alumina.

These and other objects can be obtained by the processes for the dehydrogenation of hydrocarbons, particularly aliphatic hydrocarbons, which is disclosed by the present invention.

SUMMARY OF THE INVENTION

The invention is a method of dehydrogenating a hydrocarbon feed stream, particularly a C3 to C5 alkane hydrocarbon feed stream, comprising passing the feed stream over a dehydrogenation catalyst, wherein the dehydrogenation catalyst comprises from about 50 to about 90 percent of an eta alumina carrier, from about 10 to about 30 percent by weight of a chromium compound and from about 0.1 to about 5 percent by weight of a zirconium compound, added as a stabilizing material. Other additives, such as alkali metal compounds, preferably potassium, sodium or cesium compounds, can also be added to the catalyst to enhance the process.

DETAILED DESCRIPTION OF THE INVENTION

The invention comprises a method for dehydrogenation of hydrocarbon feed stream, preferably a C3 to C5 alkane feed stream, comprising passing the feed stream over an improved dehydrogenation catalyst comprising from about 50 to about 90 percent of an eta alumina carrier, from about 10 to about 30 percent by weight of a chromium compound and from about 0.1 to about 5 percent by weight of a zirconium compound added to the catalyst as a stabilizing material. Other additives or stabilizing materials may also be added to the catalyst to enhance the method. The method has shown significant usefulness for the conversion of isobutane to isobutylene and the dehydrogenation of other hydrocarbon products, such as propanes and pentanes.

There are many types of aluminas that may be used as the carrier material for the catalyst. Conventionally, the alumina used for dehydrogenation catalysts is a porous alumina having a relatively high surface area comprising gamma-type alumina with a surface area of from about $120\ m^2/g$-$300\ m^2/g$. Alumina of this type is disclosed, for example, in U.S. Pat. No. 2,956,030.

It has been surprisingly discovered that improved dehydrogenation catalysts are produced when the alumina utilized is predominantly an eta alumina. Eta alumina carriers are conventionally produced by heating a bayerite form of aluminum trihydrate. Alternatively, the eta alumina may be acquired from alumina suppliers. However, because eta alumina is not a preferred phase for use as a carrier of catalysts, there is a limited market for this material. Most often eta alumina is produced directly from its source material, i.e., by heating the bayerite form of aluminum trihydrate.

Eta alumina is then formed into shapes acceptable for use as the carrier of the catalyst. For example, eta alumina carrier pellets with a diameter of about ⅛ inch can be formed by conventional procedures. These pellets are then dried and calcined by conventional procedures to produce a carrier with a surface area from about $100\ m^2/g$ to about $300\ m^2/g$ and preferably from about $120\ m^2/g$ to about $150\ m^2/g$.

A chromium compound is then added to the eta alumina carrier. One method of adding the chromium compound requires dipping of the eta alumina carrier into an aqueous solution of chromic acid, which is prepared by dissolving chromic oxide in water. Other chromium compounds can also be used as the source material for the chromium additive. The concentration of the chromic oxide in solution must be sufficient to load the desired amount of chromia on the carrier in a single impregnation step. The eta alumina pellets are impregnated by dipping the pellets into the chromia solution. The impregnated pellets are then dried and calcined using conventional procedures. The preferred loading of chromium oxide onto the eta alumina carrier is from about 10 to about 30 percent and more preferably from about 15 to about 25 percent.

While the catalysts may be used in this form, in a preferred embodiment, a stabilizing additive is added to the chromia-eta alumina catalyst, preferably zirconia. The chromia-eta alumina catalysts are preferably impregnated with a zirconium solution formed from a zirconium salt, such as zirconyl nitrate. Preferably, the concentration of the solution of the zirconium salt is sufficient to produce a loading of the chromia-eta alumina catalyst from about 0.1 percent to about 5 percent by weight. As a preferred alternative process to the zirconium compound being separately added to the chromia-eta alumina catalysts, the zirconium compound can be coimpregnated with the chromium compound. In this process, a zirconium salt, preferably zirconyl carbonate at the appropriate concentration, is dissolved in chromic acid and the two metals are then coimpregnated into the eta alumina carrier.

After impregnation the catalyst is dried and then calcined at conventional temperatures to form the final catalyst product. The final concentration of the zirconium oxide in the catalyst is preferably from about 0.1 to about 5 percent by weight and most preferably from about 0.1 to about 1 percent by weight.

Other additives may also be added to the catalyst of the invention, such as silica, lanthanum compounds, and alkali metal compounds, such as potassium, sodium and cesium compounds. The concentration of the additional additive on the catalyst is in the range of about 0.1 to about 5.0 percent by weight and preferably from about 0.1 to about 1.0 percent by weight.

The surface area of the formed catalyst is preferably from about $60\ m^2/g$ to about $120\ m^2/g$.

It has been surprisingly discovered that dehydrogenation catalysts made from a combination of an eta alumina impregnated with chromia and zirconia, as a stabilizer, provide improved performance over prior art dehydrogenation catalysts. Further, it has surprisingly been discovered that the catalysts of the invention perform better than catalysts produced using a conventional gamma alumina carrier. It has also been surprisingly discovered that there is a synergistic relationship in catalysts which contain both a zirconium additive and an eta alumina carrier which produces a surprisingly large improvement in the performance and stability of a catalyst made containing eta alumina, chromia and zirconium over a conventional catalyst produced from gamma alumina, chromia and zirconia. For example, it has been discovered that the performance of aged catalysts of the invention in a conventional dehydrogenation reaction at 1,050° F. (566° C.) for the conversion of isobutane to isobutylene was surprisingly better than conventional dehydrogenation catalysts produced from gamma alumina-chromia stabilized with zirconium. In addition, there was also an improvement in selectivity of the eta alumina based catalyst and ultimately an improvement in yield. Further, the catalysts of the invention were also more stable during the dehydrogenation reaction than conventional gamma alumina based catalysts. In fact, when these two types of catalysts are compared, it is clear that catalysts of the invention, comprised of chromia on an eta alumina carrier with a zirconia stabilizer, outperform similar catalysts which contain a gamma alumina carrier. Based on the teachings of the prior art that gamma alumina based catalysts outperformed eta alumina based catalysts, these were certainly surprising results.

It will be apparent from the foregoing that while particular forms of the invention have been illustrated, various modifications can be made without departing from the scope of the invention. Accordingly, it is not intended to limit the invention except by the claims.

The invention claimed is:

1. A process for the dehydrogenation of a $C_3$-$C_5$ hydrocarbon feed stream comprising
providing a dehydrogenation catalyst where the dehydrogenation catalyst comprises from about 70 to about 90 percent of eta alumina formed carrier, from about 15 to about 25 percent of a chromium compound and from about 0.1 to about 5 percent, by weight, of a zirconium compound, wherein the chromium compound and zirconium compound are impregnated on the eta alumina formed carrier;
passing an aliphatic hydrocarbon feed stream comprising $C_3$-$C_5$ compounds over the dehydrogenation catalyst; and
producing a dehydrogenated unsaturated $C_3$-$C_5$ hydrocarbon product.

2. The process of claim 1 wherein the hydrocarbon feed stream comprises isobutane.

3. The process of claim 1 wherein the hydrocarbon feed stream comprises propanes and pentanes.

4. The process of claim 1 wherein the zirconium compound comprises from about 0.1 to about 1 percent of the dehydrogenation catalyst, by weight.

5. The process of claim 1 wherein the dehydrogenation catalyst has a surface area from about 60 $m^2$/g to about 120 $m^2$/g.

6. The process of claim 1 wherein the dehydrogenation catalyst further comprises an additive selected from the group consisting of silica, lanthanum compounds, alkali metal additive and mixtures thereof.

7. The process of claim 1 wherein the dehydrogenation catalyst further comprises an alkali metal additive selected from the group consisting of potassium, sodium and cesium compounds and mixtures thereof.

8. The process of claim 1 wherein the dehydrogenation catalyst is prepared by impregnating the eta alumina formed carrier with the chromium compound and with the zirconium compound in separate steps.

9. The process of claim 1 wherein the dehydrogenation catalyst is prepared by co-impregnating the eta alumina formed carrier with the chromium compound and the zirconium compound in a single step.

10. A process for the dehydrogenation of a $C_3$-$C_5$ hydrocarbon feed stream comprising
providing a dehydrogenation catalyst where the dehydrogenation catalyst comprises from about 70 to about 90 percent, by weight, of eta alumina formed carrier, from about 15 to about 25 percent, by weight, of a chromium compound, from about 0.1 to about 1 percent by weight of a zirconium compound, and an additive selected from the group consisting of silica, lanthanum compounds, and alkali metal additives and mixtures thereof, wherein the chromium compound and zirconium compound are impregnated on the eta alumina formed carrier;
passing an aliphatic hydrocarbon feed stream comprising $C_3$-$C_5$ compounds over the dehydrogenation catalyst; and
producing a dehydrogenated unsaturated $C_3$-$C_5$ hydrocarbon product.

11. The process of claim 10 wherein the hydrocarbon feed stream comprises isobutane.

12. The process of claim 10 wherein the hydrocarbon feed stream comprises propanes and pentanes.

13. The process of claim 10 wherein the zirconium compound comprises from about 0.1 to about 1 percent of the dehydrogenation catalyst, by weight.

14. The process of claim 10 wherein the dehydrogenation catalyst has a surface area from about 60 $m^2$/g to about 120 $m^2$/g.

15. The process of claim 10 wherein the alkali metal additive is selected from the group consisting of potassium, sodium and cesium compounds and mixtures thereof.

16. The process of claim 10 wherein the dehydrogenation catalyst is prepared by impregnating the eta alumina formed carrier with the chromium compound and with the zirconium compound in separate steps.

17. The process of claim 10 wherein the dehydrogenation catalyst is prepared by co-impregnating the eta alumina formed carrier with the chromium compound and the zirconium compound in a single step.

* * * * *